United States Patent [19]

Login et al.

[11] Patent Number: 5,183,901

[45] Date of Patent: Feb. 2, 1993

[54] UREA-HYDROGEN PEROXIDE-POLYVINYLPYRROLIDONE

[75] Inventors: Robert B. Login, Oakland; John J. Merianos, Middletown; Russell B. Biss, Paramus; Paul Garelick, South Plainfield, all of N.J.

[73] Assignee: ISP Investments Inc., Wilmington, Del.

[21] Appl. No.: 825,359

[22] Filed: Jan. 24, 1992

[51] Int. Cl.$^5$ .............................................. C01B 15/01
[52] U.S. Cl. ................................. 548/543; 524/438; 423/272; 423/265; 252/186.29
[58] Field of Search .................... 548/543; 524/438

[56] References Cited

U.S. PATENT DOCUMENTS 3,376,110  4/1968  Shiraeff et al. ................ 23/207.5
5,008,293  4/1991  Merianos ........................ 548/543

FOREIGN PATENT DOCUMENTS 3444552  6/1986  Fed. Rep. of Germany.

*Primary Examiner*—David B. Springer
*Attorney, Agent, or Firm*—Walter Katz; Marilyn J. Maue; Joshua J. Ward

[57] ABSTRACT

Urea-hydrogen peroxide-polyvinylpyrrolidone (PVP) in the form of a free-flowing powder is stable against decomposition in water and alcohol solvents. The product is obtained by spraying an aqueous solution of urea-hydrogen peroxide onto a fluidized bed of PVP and drying; it contains about 5%-20% by weight $H_2O_2$ and less than about 5% water. The urea-hydrogen peroxide solution is applied onto the fluidized PVP bed at a predetermined rate, suitably about 0.5-30 g of solution/minute/kg PVP in the bed, and, preferably, about 1-3 g/min/kg PVP.

13 Claims, No Drawings

UREA-HYDROGEN PEROXIDE-POLYVINYLPYRROLIDONE

BACKGROUND OF THE INVENTION

1. Field of the Invention

This invention relates to urea-hydrogen peroxide stabilized towards decomposition in an aqueous or alcoholic solution, and, more particularly, to free-flowing powders of a urea-hydrogen peroxide-PVP product made by a fluid bed process.

2. Description of the Prior Art

Urea-hydrogen peroxide is a well-known commercial product useful as an antiseptic and disinfectant in treatment of wounds, for bleaching hair, and as a readily biodegradable and environmentally safe bleaching agent, detergent and cleaning agent. However, urea-hydrogen peroxide, also known as carbamide-peroxide, is not very stable in aqueous and alcoholic solutions. Several techniques have been used in an attempt to provide stabilized carbamide peroxide solutions; for example, see U.S. Pat. Nos. 2,120,430; 2,430,450; 2,542,898; 3,629,331; 3,657,413; 4,155,738; 4,302,441; 4,514,384; 4,518,583; 4,522,805; 4,607,101; 4,826,681; 4,837,008 and 4,895,875. However, these methods have not been entirely successful; accordingly, it is recommended that carbamide peroxide remain refrigerated during periods of non-use.

Stabilized $H_2O_2$ compositions also have found wide utility in commercial and industrial applications, e.g. as an antiseptic, disinfectant, sterilization agent, bleaching material, washing concentrate, etchant, in cosmetic preparations, and as a catalyst in polymerizations requiring a free radical source. In biological applications which require an antiseptic, disinfectant or sterilization agent, such $H_2O_2$ compositions require release of an effective amount of oxygen at a desired rate.

Shiraeff, in U.S. Pat. Nos. 3,376,110 and 3,480,557, disclosed that a solid, stabilized hydrogen peroxide composition of hydrogen peroxide and a polymeric N-vinyl heterocyclic compound could be prepared from an aqueous solution of the components. The process involved mixing PVP and a substantial excess of aqueous $H_2O_2$ and evaporating the solution to dryness. The $H_2O_2$ content of the composition was given as being at least 2%, and preferably 4.5 to 70% by weight. Prolonged drying of the composition, in an attempt to reduce the water content, however, resulted in a substantial loss of $H_2O_2$ from the complex. The product was a brittle, transparent, gummy, amorphous material, and had a variable $H_2O_2$ content ranging from about 3.20 to 18.07% by weight, depending upon the drying times.

The Shiraeff process did not attain commercial success because (1) the product was not a free-flowing powder and thus could not be handled easily; (2) its water and hydrogen peroxide content varied over a wide range; (3) the complex was not stable; and (4) the aqueous process could not be carried out on a commercial scale.

Merianos, in U.S. Pat. No. 5,008,093 described an improved process for making free-flowing, substantially anhydrous complexes of PVP and $H_2O_2$ by reacting PVP and a solution of $H_2O_2$ in an anhydrous organic solvent such as ethyl acetate. However, this process required the use of substantially anhydrous $H_2O_2$, which was too dangerous to handle industrially.

Rossberger et al., in German Patent OLS 3,444,552, published Jun. 12, 1986, described a process for making urea peroxyhydrate using a fluidized bed of urea having a particle size of less than 1000 $\mu$m onto which was sprayed an aqueous solution of concentrated $H_2O_2$. This technique was practical only because urea is a stable, crystalline compound which readily formed a free-flowing powdery complex upon addition of aqueous hydrogen peroxide solutions.

Production of free-flowing complexes of PVP-$H_2O_2$ from amorphous, polymeric, polyvinylpyrrolidone and aqueous $H_2O_2$, however, has not been easy to achieve commercially because, during production, the PVP polymer can alter its physical state, and/or retain excess water and/or free $H_2O_2$, even at elevated drying temperatures, resulting in a gummy rather than a free-flowing product.

Accordingly, it is an object of this invention to provide free-flowing powders of urea-hydrogen peroxide-PVP which exhibits stability towards decomposition in aqueous and alcoholic solutions.

Still another object is to provide a free-flowing powders of urea-hydrogen peroxide-PVP made by spraying an aqueous solution of urea-hydrogen peroxide onto a fluidized bed of PVP at a predetermined rate, and drying.

These and other objects and features of the invention will be made apparent from the following description herein.

SUMMARY OF THE INVENTION

What is described herein is a urea-hydrogen peroxide-polyvinylpyrrolidone product in the form of a free-flowing powder. In the preferred embodiment of the invention, this product has a hydrogen peroxide content of about 5% to 20% by weight. Most preferably with a water content of less than 5%. The product is non-hydroscopic at room temperature and stabilized towards decomposition in water and alcoholic solutions. The process herein for the production of free-flowing powders of a urea-$H_2O_2$-PVP product comprising reacting a fluidized bed of PVP maintained at a reaction temperature of from ambient temperature to about 60° C. with finely divided droplets of a 20 to 50% by weight aqueous solution of a urea-$H_2O_2$, and drying the product.

DETAILED DESCRIPTION OF THE INVENTION

In accordance with the present invention, a fluidized bed containing a charge of PVP powders is reacted with an aqueous solution of concentrated urea-hydrogen, peroxide, suitably a 15-30% by weight urea-hydrogen peroxide solution, preferably about 20%.

The fluidized bed of PVP powders can be maintained in the fluidized condition by directing a current of dry air through the powders, by mechanical agitation of the powders, or by a combination of both techniques.

The fluidized bed also is maintained at a suitable bed (reaction) temperature at which formation of the desired urea-$H_2O_2$-PVP product can occur readily without affecting the powdery state of the polymer, and at which temperature excess water can be removed quickly from both the product and the bed itself. The selected bed temperature also will enhance the formation of the desired product in the form of a free-flowing powder rather than a gum. Such suitable reaction temperature ranges from ambient temperature to about 60° C., preferably about 35° to 50° C.

The aqueous, concentrated urea-$H_2O_2$ solution preferably is contacted with the PVP powders as finely divided droplets of liquid. Such desired droplets may be formed by pumping the urea-$H_2O_2$ solution through a spray nozzle and onto the polymer bed at a selected rate and for a predetermined period of time. Any spray nozzle capable of producing a fine dispersion of droplets may be used for this purpose. If necessary, however, a stream of air may be introduced into such nozzle with the solution to assist in atomizing the solution into finely divided droplets.

The spray solution of aqueous urea-$H_2O_2$ thus formed preferably is introduced into the fluidized bed of PVP polymer powders at a selected rate such that excess water can be removed therein during formation of the complex without retaining an unreasonable amount of free $H_2O_2$ therein. A suitable feed rate for introduction of the urea-$H_2O_2$ solution in a peroxide concentration of 15–30% is about 1–10 g of the urea-$H_2O_2$ solution/minute/kg copolymer, preferably about 2-5 g solution/minute/kg PVP polymer. Under these selected flow rate conditions, a stable, free-flowing powder of the desired urea-$H_2O_2$-PVP complex is obtained which contains about 5–20% $H_2O_2$, and about 5% or less water.

In the preferred form of the process of the invention, the spray solution of urea-$H_2O_2$ is directed onto the PVP polymer bed for a period sufficient to form a free-flowing powder having an $H_2O_2$ content of about 5% to 20% by weight, which corresponds approximately to a complex having about a 1:1 molar ratio of PVP polymer to urea-$H_2O_2$. At this point in the process, the feed is discontinued to preclude the formation of excess water and/or free $H_2O_2$ on the free-flowing powder which could cause it to become gummy. The appearance of a gummy product is indicative of the presence of undesired excess water and/or free $H_2O_2$ in the product.

The spray solution of urea-$H_2O_2$ may be directed onto the fluidized bed as a vertical, horizontal or by downward flow of droplets.

If a fluidizing air stream is used to create the fluid bed, it is usually directed upwardly against the PVP polymer powders. Such air currents also can assist in carrying water away from the bed. An exhaust suction system also may be used to aid in removal of water in the air stream. The fluidized state of the bed also may be maintained using mechanical agitation, or a combination of both air and mechanical means.

The process of the invention can be carried out in one or two steps, i.e. removal of water from the product and bed can take place (a) simultaneous with, or after mixing, of the reaction components in the same apparatus, or (b) in a downstream drying step, or (c) by a combination of both steps. The particular method of drying will depend upon the type of equipment used. For example, if a fluidized bed mixer is used, such as a plowshare, belt screw or paddle mixer, then the moist urea-$H_2O_2$-PVP product can be dried further in a separate dryer. This sequence is characterized as a two-step process. Any suitable dryer can be used for this purpose, such as a vacuum, radiant heat or contact dryer.

Furthermore, if desired, application of the spray urea-$H_2O_2$ solution onto the PVP polymer bed, followed by downstream drying, may be carried out in several stages in order to increase the $H_2O_2$ content of the product towards the desired 1:1 molar ratio, and to reduce its water content.

Moreover, a fluid bed dryer may be used in the process which has the dual capabilities of providing both the fluidized bed and drying functions. Accordingly, drying of the product will begin and be completed during reaction between the copolymer charge and the aqueous urea-$H_2O_2$ solution. Such a process may be considered as taking place in a one-step.

Preferably, reaction and dehydration are continued until the product reaches the desired $H_2O_2$ content, suitably about 5–20% $H_2O_2$, with less than about 5% water. Moreover, it is essential that the product remain in the desired free-flowing state after completion of addition of the $H_2O_2$ solution and drying.

The size of the fluidized bed reactor, the rate of addition of the urea-hydrogen peroxide solution, and the reaction time will depend upon the particular equipment used, as well as the concentration of the urea-hydrogen peroxide solution and the reaction temperature, keeping in mind the purposes intended to be achieved with respect to each of these process parameters. However, it is believed that the following examples will illustrate the employment of process condition which enable the production of the desired free-flowing, stable urea-$H_2O_2$-PVP powder product. These examples, of course, are given by way of illustration only, and are not to be construed as limiting the invention.

EXAMPLE 1

A fluid bed dryer apparatus was charged with 500 g of PVP. Then 250 g of an aqueous solution of urea-hydrogen peroxide (34% by weight $H_2O_2$) in a concentration of 20% of the solution in an air stream was sprayed through a nozzle onto the charged fluidized bed of PVP at 50° C. at the rate of 2 g of the solution/min/kg PVP. A vacuum was maintained in the system during the addition of solution which continuously removed water from the product into the air stream. Subsequently, the product was dried for 22 hours at 50° C. under reduced pressure. 575 g of a free-flowing powder was obtained which contained 14.78% $H_2O_2$ and 4.3% water.

EXAMPLE 2

The product of Example 1 was tested for stability against decomposition in water, ethanol and propylene glycol, and compared with unstabilized urea-hydrogen peroxide. After accelerated testing at 40° C. for 18 months, only 20% $H_2O_2$ was lost from the urea-hydrogen peroxide-PVP product of Example 1, whereas, under these conditions, urea-hydrogen peroxide decomposed completely, and no $H_2O_2$ activity remained.

The product of the invention can be used in applications where the disinfectant and/or bleaching property of $H_2O_2$ is desired. In a hair cosmetic composition, for example, the conditioning property of PVP can provide the product with the dual action of bleaching and hair conditioning. Besides other personal care products for oral cavity such toothpaste and topical disinfection solution can be prepared from this stabilized solid form of hydrogen peroxide.

The presence of PVP stabilizes the urea-$H_2O_2$ complex in such solvents as water, alcohol and propylene glycol, and mixtures thereof, as compared to untreated urea-$H_2O_2$ itself. Accelerated testing of urea-$H_2O_2$-PVP at 40° C. indicated that the product had an 18 month shelf-life, and lost only 20% of its peroxide activity, whereas urea-$H_2O_2$ was hydroscopic and required refrigeration to prevent substantial decomposition at room temperature.

While the invention has been described with particular reference to certain embodiments thereof, it will be understood that changes and modifications may be made which are within the skill of the art. Accordingly, it is intended to be bound only by the following claims, in which:

What is claimed is:

1. A process for the production of free-flowing powders of a urea-$H_2O_2$-PVP product comprising reacting a fluidized bed of PVP maintained at a reaction temperature of from ambient temperature to about 60° C. with finely divided droplets of a 15 to 30% by weight aqueous solution of urea-$H_2O_2$, and drying the product.

2. A process according to claim 1 wherein said solution is introduced at a selected feed rate such that excess water can be removed during formation of said product.

3. A process according to claim 1 wherein introduction of said solution is carried out under vacuum and is continued until the resultant product contains about 5 to 20% by weight hydrogen peroxide.

4. A process according t claim 2 wherein the feed rate of the urea-$H_2O_2$ solution is about 1-10 g of solution/minute/kg PVP.

5. A process according t claim 1 wherein said reaction temperature is about 35° to 50° C.

6. A process according to claim 1 wherein about a 20% urea-$H_2O_2$ solution is used and the urea-$H_2O_2$ reactant contains about 34% $H_2O_2$.

7. A process according to claim 6 wherein said solution feed rate is about 2-5 g of solution/minute/kg copolymer.

8. A process according to claim 1 wherein drying is carried out in the fluidized bed during formation of the product, or in a downstream dryer.

9. A process according to claim 8 wherein both said reaction and drying steps are carried out in a fluidized bed dryer.

10. A process according to claim 8 wherein the reaction is carried out in a fluidized bed reactor, and further drying of the wet product is performed in a downstream dryer.

11. A process according to claim 1 wherein air is used to fluidize the copolymer powders and to assist in removing water from the fluidized bed during the process.

12. A process according to claim 1 wherein the product contains about 5% or less water therein.

13. A process according to claim 1 wherein air is used to assist in forming spray droplets of the urea-$H_2O_2$ solution.

* * * * *